United States Patent [19]
Prasad

[11] Patent Number: 5,536,527
[45] Date of Patent: Jul. 16, 1996

[54] METHOD AND APPARATUS FOR APPLYING COATING TO SURGICAL NEEDLES

[75] Inventor: Janniah S. Prasad, Norwalk, Conn.

[73] Assignee: American Cyanamid Company, Wayne, N.J.

[21] Appl. No.: 298,266

[22] Filed: Aug. 31, 1994

[51] Int. Cl.⁶ .................. B05D 1/28; B05D 5/08; A61M 5/178
[52] U.S. Cl. .................. 427/2.28; 427/365; 427/429; 427/368; 118/106; 118/257
[58] Field of Search .................. 427/11, 2.28, 242, 427/178, 428, 429, 363, 365, 384, 368, 156; 118/257, 106, 70

[56] References Cited

U.S. PATENT DOCUMENTS

| | | | |
|---|---|---|---|
| 2,868,162 | 1/1959 | Knain | 118/257 |
| 3,083,683 | 4/1963 | Fischer et al. | 118/106 |
| 3,574,673 | 8/1971 | Schweiger et al. | 117/132 |
| 3,695,223 | 10/1972 | Dunham et al. | 118/257 |
| 4,030,444 | 6/1977 | Collins et al. | 118/257 |
| 4,104,985 | 8/1978 | Klein | 118/257 |
| 4,321,885 | 3/1982 | Wallace | 118/106 |
| 4,462,880 | 7/1984 | Hill et al. | 427/558 |
| 4,509,981 | 4/1985 | Sanders, Jr. et al. | 106/3 |
| 4,534,363 | 8/1985 | Gold | 128/772 |
| 4,720,521 | 1/1988 | Spielvogel et al. | 624/862 |
| 4,791,029 | 12/1988 | Fau et al. | 428/447 |
| 4,806,430 | 2/1989 | Spielvogel et al. | 428/450 |
| 4,844,986 | 7/1989 | Karakelle et al. | 428/447 |
| 4,905,695 | 3/1990 | Bendel et al. | 606/222 |
| 4,959,068 | 9/1990 | Bendel et al. | 606/222 |
| 5,258,013 | 11/1993 | Granger et al. | 606/223 |
| 5,456,948 | 10/1995 | Mathisen et al. | 427/2.28 |

FOREIGN PATENT DOCUMENTS

| | | | |
|---|---|---|---|
| 0131163A1 | 12/1984 | European Pat. Off. | C09D 3/82 |
| 0500229A1 | 4/1992 | European Pat. Off. | |

OTHER PUBLICATIONS

Derwent Abstract of JP 3080869, Apr., 1991.

*Primary Examiner*—Diana Dudash
*Attorney, Agent, or Firm*—Montgomery W. Smith; Charles F. Costello; Rita D. Vacca

[57] ABSTRACT

A method and apparatus for applying a lubricant coating to surgical needles utilizes a belt coating system with two endless belts. The endless belts have confronting running sides and are rotated in opposite directions for feeding the surgical needles therebetween. The needles are fed between the confronting running sides and are pressed lightly between the endless belts, whose surfaces have been wetted with the lubricant solution. The needles are cured after coating.

17 Claims, 1 Drawing Sheet

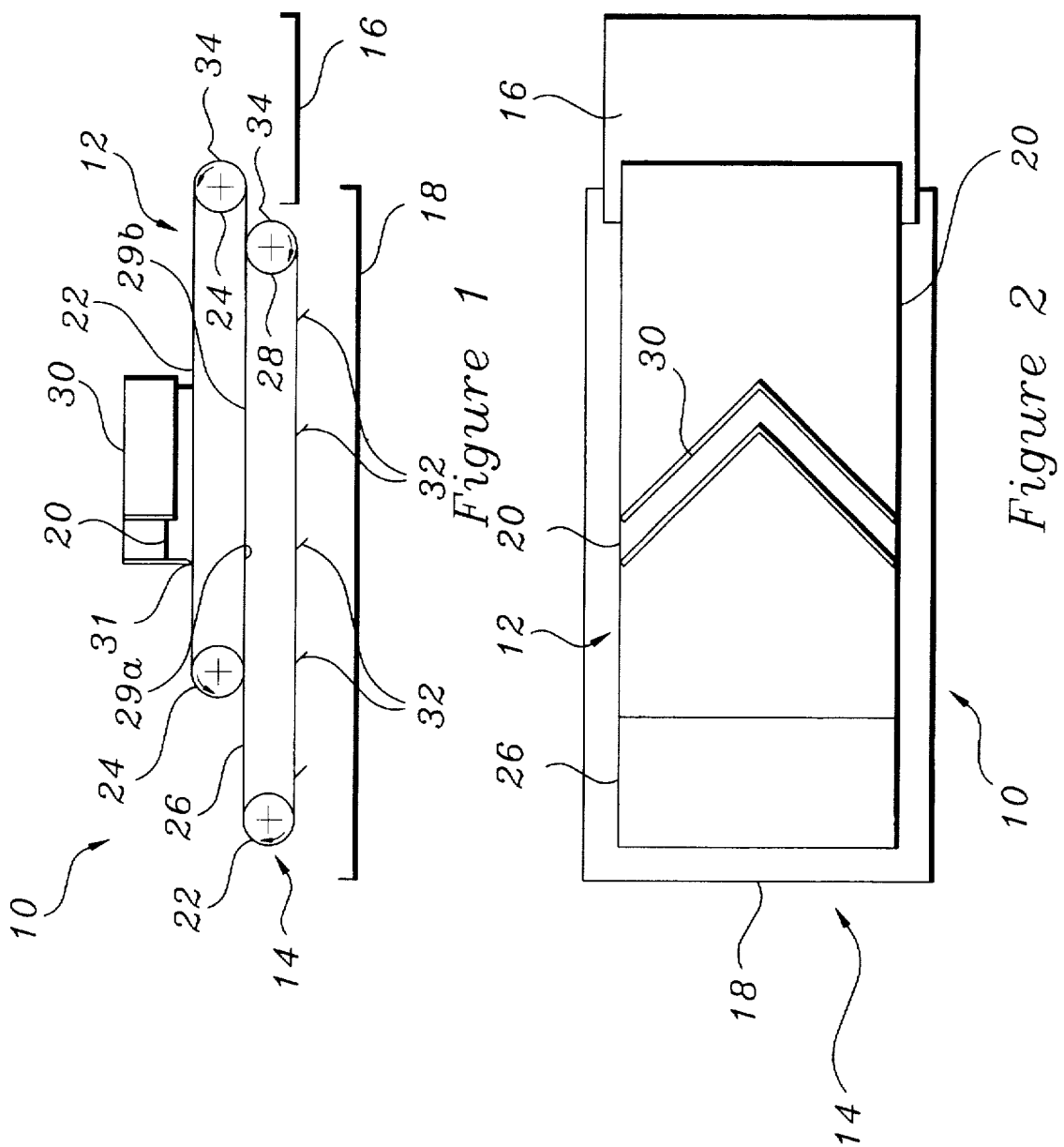

METHOD AND APPARATUS FOR APPLYING COATING TO SURGICAL NEEDLES

BACKGROUND OF THE INVENTION

1. Field of the Invention

The invention relates generally to a system for coating needles, and more particularly, to a method and apparatus for applying a lubricant coating to surgical needles used in the medical field.

Surgical needles are used by doctors and other medical professionals to apply sutures, or stitches, by hand through a patient's skin or tissue. Typically, the sutures are used to close wounds or adjoin adjacent tissue, often at the conclusion of a surgical procedure. Coating the surgical needles with a thin layer of lubricant is done to enhance the performance of the needle.

2. Description of the Prior Art

It has long been known to apply a lubricant coating to surgical needles. The primary advantage of applying a lubricant, such as a silicone-based solution, is that it reduces friction between the needle and the tissue. This reduction of friction lessens the so-called "drag-force" of the needle passing through the tissue and reduces the pain and discomfort felt by the patient. A lower drag-force also lessens tissue trauma, or in other words, damage to the tissue caused by the needle passage. Less tissue trauma results in reduced healing time for the patient. Although surgical needles are generally disposed of after use in a given surgical procedure, an effective lubricant solution should stay on the needle for however many passes the needle makes through the tissue during its single use.

There are several well-known methods of applying a lubricant coating to surgical needles. Perhaps the most basic method is simply dipping the needles in a lubricant solution. However, this method is slow and tedious, resulting in poor production output. An updated method of applying the lubricant coating is to spray the surgical needles using an atomizer. The atomizer mixes a lubricant solution with large amounts of air and sprays, or atomizes, the surgical needles. However, spraying results in a considerable amount of wasted solution, which increases the cost. Another drawback of spraying is that the mixing of the lubricant solution with large amounts of air makes combustion of the atomized solution a genuine concern. Therefore, the dilutants to be mixed with the lubricant must be limited to non-combustible materials. Spraying can also be time consuming because, unless the needles are suspended, they can only be sprayed one side at a time.

It would be desirable to provide an improved method and apparatus for applying a lubricant coating to surgical needles that did not have the drawbacks of conventional methods.

SUMMARY OF THE INVENTION

It is a general object of the invention to provide an improved method and apparatus for applying a lubricant coating to surgical needles.

It is another object of the invention to provide an efficient and economical method and apparatus for applying the lubricant coating to the surgical needles.

It is still another object of the invention to provide a method and apparatus for positively coating the surgical needles with a lubricant coating.

It is yet another object of the invention to provide a method and apparatus for applying a lubricant coating to the needle that has a high production output.

In accordance with one aspect of the invention, a method for coating surgical needles uses a belt coating device with first and second endless belts disposed to have confronting running sides. The method comprises the steps of rotating the first and second endless belts in opposite directions, wetting outer surfaces of the endless belts with a lubricant solution, feeding the surgical needles between the confronting running sides of the endless belts, and coating the needles with the lubricant solution as they travel between the coated surfaces of the endless belts.

In accordance with another aspect of the invention, a method for coating suture needles comprises the steps of providing an apparatus having upper and lower endless belts mounted to have confronting running sides, rotating the upper and lower belts in opposite directions to provide a path for transporting the surgical needles between the upper and lower endless belts, wetting the outer surfaces of the endless belts with a lubricant solution for coating the surgical needles, and feeding the surgical needles between the endless belts so the needles are pressed lightly between the wetted surfaces.

In accordance with another aspect of the invention, a sponge and a trough-like sponge container are positioned above the upper endless belt to contain and transfer the lubricant solution.

In accordance with yet another aspect of the invention, the upper and lower endless belts are offset from one another so the needles can be easily fed to the lower endless belt.

In accordance with still another aspect of the invention, an apparatus for coating surgical needles comprises an upper endless belt, a lower endless belt disposed to have a common running side with the upper endless belt, and means for applying a solution to an outer surface of the endless belts. The upper and lower endless belts are rotated in opposite directions and surgical needles are fed between the rotating belts to be coated with the solution.

These and other objects, aspects, features and advantages of the present invention will become apparent from the following detailed description of the preferred embodiments taken in conjunction with the drawings.

BRIEF DESCRIPTION OF THE DRAWINGS

FIG. 1 is a side elevational view of a belt coating apparatus in accordance with the present invention;

FIG. 2 is a top plan view of the belt coating apparatus shown in FIG. 1.

DESCRIPTION OF THE PREFERRED EMBODIMENTS

Generally, the subject invention relates to a method and apparatus for applying a lubricant solution to surgical needles using a belt coating system. The system uses two endless belts positioned to contact each other along confronting running sides. A lubricant solution is applied to wet the outer surfaces of the endless belts. Surgical needles are then fed along the common running side and pressed lightly between the endless belts to coat the needles with the lubricant solution. The needles are collected in a tray as they exit the endless belts and then cured.

One example of a belt coating system 10 used for practicing the subject method of applying a lubricant solution is shown in FIGS. 1 and 2. The primary elements of the system 10 include an upper belt assembly 12, a lower belt assembly 14, a needle collection tray 16, a drip tray 18 and a sponge 20.

The upper belt assembly 12 is comprised of an endless belt 22 formed as a closed loop and reeved around two rollers 24. Similarly, the lower belt assembly 14 has an endless belt 26 forming a closed loop and reeved around two rollers 28. The dimensions of the belts can vary and will depend on the desired size and output capability of the device. However, typical dimensions will find the endless belts to be approximately 14 inches to 16 inches in length (roller to roller) and 4 inches in width. The rollers 24 and 28 can be, for example, 1 inch in diameter and preferably have a length comparable to the width of the belts. The endless belts are readily available commercial-grade belts and should be non-absorbable, preferably with a textured outer surface for retaining, or holding, small amounts of the lubricant solution.

As best seen in FIG. 1, the upper and lower belts should be positioned to have confronting running sides, or surfaces, 29a and 29b. More specifically, the upper belt assembly 12 is supported just above the lower belt assembly 14 such that a bottom surface 29a of the upper endless belt 22 contacts a top surface 29b of the lower endless belt 26. As will be appreciated, the upper and lower endless belts are rotated in opposite directions such that the confronting running surfaces 29a and 29b are travelling in the same direction. In the embodiment shown in FIG. 1, the rollers 24 of the upper belt assembly are rotated counter-clockwise about their longitudinal axis, and the rollers 28 of the lower belt assembly are rotated clockwise about their longitudinal axis. As is conventional, typically only one of the rollers in each belt assembly serves as a driving roller and is rotated by unshown driving means, and the other roller is driven, or rotated, by the endless belt.

As evident in both FIGS. 1 and 2, the belt assemblies are laterally offset, with the lower belt assembly 14 being disposed slightly forwardly from the upper belt assembly 12 (with respect to the travel direction of the running surface, that is, with the inlet end considered "forward" and the outlet end considered "rearward"). This offset arrangement makes it easier to feed the surgical needles between the belt assemblies as discussed in more detail below. Extending the upper belt assembly past the rearward end of the lower belt assembly also aids in dispensing the coated surgical needles into the collection tray. The porous sponge 20 is provided in a trough-like sponge container 30 supported above the upper belt assembly 12 and serves as a transfer medium for transferring the lubricant solution to the upper endless belt 22. As best seen in FIG. 2, the sponge 20 and container 30 are preferably V-shaped to allow for a greater surface area of the sponge to contact the upper endless belt and produce a thorough application of the lubricant solution. Of course, other means for wetting the endless belts with the lubricant solution are within the scope of the invention.

With reference to FIG. 1, a forward end scraper or doctor blade 31 of the container extends downwardly and contacts the upper endless belt 22 to prevent excess lubricating solution from being applied.

The drip tray 18 is disposed beneath the lower belt assembly 14 to collect excess lubricant solution that runs off the belt coating system. As shown in the figures, the drip tray is preferably slightly wider than the endless belts and extends past the forward end of the lower belt assembly 14. Fins 32 are provided below the lower surface of the lower endless belt 26 to continually clean, by gently scraping, the lower endless belt. The fins are preferably supported by an unshown spring-loaded mechanism on a frame of the system and biased against the lower endless belt. Fins 34 can also be biased against the rearward ends of the upper and lower endless belts. These fins also continually clean the endless belts, but in addition help to remove any surgical needles adhered to the upper or lower endless belts and guide the needles into the collection tray 16. Fins 34 are also supported by an unshown spring-loaded mechanism on the frame of the belt coating system. Other comparable means for cleaning and/or removing the coated needles from the endless belts can be provided without departing from the scope of the present invention.

The collection tray 16 is positioned at the rearward, or exit, end of the belt coating device 10 for receiving the coated surgical needles as they exit from between the endless belts. As shown in FIG. 2, the collection tray is also wider than the endless belts.

An example of using the belt coating system for applying a lubricant solution to the surgical needles in accordance with the subject invention will be discussed below.

In preparation for coating the surgical needles, a lubricant solution is dispensed into the trough-like container 30 to soak the porous sponge 20. Many well-known lubricant solutions can be used in practicing the method of the subject invention. For example, an aqueous silicone coating solution with a silicone concentration of 16% non-volatile content provides excellent results.

The upper and lower endless belts 22 and 26 are driven in opposite directions by appropriate drive means (unshown), as discussed above, at approximately 45 inches per minute. With the sponge 20 in direct contact with the upper endless belt as shown in FIG. 1, the lubricant solution is transferred to the upper belt surface as it travels in a right-to-left direction across the sponge. The forward end scraper 31 of the container prevents excess amounts of lubricant solution from being applied. As the upper and lower endless belts contact each other along the confronting running sides 29a and 29b, lubricant solution is transferred to the outer surface of the lower endless belt 24 from the upper endless belt 22. To coat the surgical needles in accordance with the subject invention, one or more needles are placed on the upper surface at the forward end of the lower endless belt 26. Since the lower endless belt is offset from the upper endless belt 22, the needles can be easily placed on the lower endless belt without interference from the upper endless belt. Once the needles are placed on the lower endless belt, they are fed in the left-to-right direction, with respect to FIG. 1, between the confronting running sides 29a and 29b between the upper and lower endless belts.

The needles are then pressed lightly between the upper and lower endless belts. Since both endless belts are coated with the lubricant solution, the solution contacts both sides of the needles and the needles are completely coated. As the needles exit the confronting running sides at the rearward ends of the upper and lower endless belts, they are fed into the curing tray 16. Fins 34 assist in removing the coated needles from the belts if necessary. Fins 32 below the lower endless belt 26 continuously scrape off excess lubricant solution and allow the solution to fall into the drip tray.

The automatic operation of the belt coating system allows surgical needles to be continuously fed through lubricant-coated upper and lower endless belts. This results in a very high output of completely coated surgical needles. It will also be appreciated that besides coating surgical needles, staples or other similar items can be coated in the same manner to achieve the same benefits. There is also a very efficient use of lubricant solution since the amount applied to the upper and lower endless belts can be regulated by the amount of solution dispensed to the porous sponge 20 and the position of the forward end scraper 31 on the container. The excess solution collected in the drip tray can also be recycled and used again if desired.

After the coated needles are deposited in the curing tray, they are cured, for example, at 150° C. for two hours.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A method for coating surgical needles using a belt coating device with first and second endless belts each having a forward and and a rearward end and disposed to have confronting running sides, said method comprising the steps of:

rotating the first and second endless belts in opposite directions;

wetting outer surfaces of the endless belts with a lubricant solution;

feeding the surgical needles between the confronting running sides between the endless belts; and coating the needles with the lubricant solution as they travel from the forward ends to the rearward ends between the wetted surfaces of the first and second endless belts.

2. A method according to claim 1, further comprising the step of wetting the outer surface of the first endless belt with a sponge disposed to be in contact with the first endless belt and containing the lubricant solution.

3. A method according to claim 2, further comprising the step of regulating the amount of lubricant solution applied by the sponge to the first endless belt.

4. A method according to claim 1, further comprising the step of catching the coated surgical needles with a tray as they exit from between the first and second endless belts.

5. A method according to claim 1, further comprising the step of cleaning the second endless belt by continuously removing excess lubricant solution therefrom.

6. A method according to claim 5, further comprising the step of collecting the excess lubricant coating removed in the cleaning step.

7. A method according to claim 1, further comprising the step of scraping the rearward ends of the first and second endless belts to remove any coated surgical needles adhered thereto.

8. A method for coating surgical needles comprising the steps of:

providing an apparatus having upper and lower endless belts mounted to have confronting running sides with an entry end and an exit end;

rotating the upper and lower endless belts in opposite directions for transporting surgical needles disposed therebetween along the confronting running sides and in a transport direction;

wetting the outer surfaces of the upper and lower endless belts with a lubricant solution for coating the surgical needles; and feeding the surgical needles along the confronting running sides between the upper and lower belts such that the needles are pressed between the wetted surfaces and coated with a layer of lubricant solution.

9. A method according to claim 8, further comprising the steps of:

providing a sponge positioned above and in contact with the upper endless belt;

applying the lubricant solution to the sponge; and running the upper endless belt across the sponge to transfer the lubricant solution thereto.

10. A method for coating surgical needles comprising the steps of:

providing an apparatus having upper and lower endless belts mounted to have confronting running sides with an entry end and an exit end;

rotating the upper and lower endless belts in opposite directions for transporting surgical needles disposed therebetween along the confronting running sides and in a transport direction;

wetting the outer surfaces of the upper and lower endless belts with a lubricant solution for coating the surgical needles;

feeding the surgical needles along the confronting running sides between the upper and lower belts such that the needles are pressed between the wetted surfacer and coated with a layer of lubricant solution;

providing a sponge positioned above and in contact with the upper endless belt;

applying the lubricant solution to the sponge;

running the upper endless belt across the sponge to transfer the lubricant solution thereto;

providing a container for holding the sponge; and preventing excess solution from being applied to the upper endless belt by providing a scraper on a forward end of the container with respect to the transport direction.

11. A method according to claim 10, further comprising the step of shaping the sponge and the container to have a linear length that is greater than a width of the upper endless belt.

12. A method according to claim 8, further comprising the steps of:

providing a curing tray at the exit end of the confronting running sides; and catching the coated surgical needles exiting from between the upper and lower endless belts.

13. A method according claim 8, further comprising the steps of:

providing fins biased against a lower surface of the lower endless belt; and continuously cleaning the lower endless belt with the fins to remove excess solution.

14. A method according to claim 13, further comprising the steps of:

providing a drip tray beneath the lower endless belt; and collecting the excess solution removed by the fins.

15. A method according to claim 8, further comprising the steps of:

providing fins at rearward ends of the upper and lower belts; and scraping the rearward ends of the upper and lower belts to remove any coated needles adhered to the endless belts.

16. A method according to claim 8, further comprising the steps of laterally offsetting the upper and lower endless belts to position the lower endless belt forward of the upper endless belt.

17. A method according to claim 11, wherein the sponge and the container are substantially V-shaped, with an angled portion of the V-shaped container disposed closest to the exit end for increasing the surface area of the sponge contacting the upper endless belt.

* * * * *